US009861575B2

(12) United States Patent
Abiko et al.

(10) Patent No.: US 9,861,575 B2
(45) Date of Patent: Jan. 9, 2018

(54) VITAMIN-CONTAINING NUTRITION INFUSION FOR ADMINISTRATION THROUGH PERIPHERAL VEIN

(71) Applicant: AJINOMOTO CO., INC., Chuo-ku (JP)

(72) Inventors: Kazuhiro Abiko, Shizuoka (JP); Toshiyuki Katsura, Shizuoka (JP)

(73) Assignee: EA Pharma Co., Ltd., Chuo-ku (JP)

( * ) Notice: Subject to any disclaimer, the term of this patent is extended or adjusted under 35 U.S.C. 154(b) by 0 days.

(21) Appl. No.: 13/668,558

(22) Filed: Nov. 5, 2012

(65) Prior Publication Data

US 2013/0078228 A1  Mar. 28, 2013

Related U.S. Application Data

(63) Continuation of application No. PCT/JP2011/060899, filed on May 2, 2011.

(30) Foreign Application Priority Data

May 7, 2010 (JP) ................................ 2010-107429

(51) Int. Cl.
| | |
|---|---|
| *A61K 9/08* | (2006.01) |
| *A61K 9/00* | (2006.01) |
| *A61K 31/197* | (2006.01) |
| *A61K 31/375* | (2006.01) |
| *A61K 31/4188* | (2006.01) |
| *A61K 31/4415* | (2006.01) |
| *A61K 31/455* | (2006.01) |
| *A61K 31/51* | (2006.01) |
| *A61K 31/525* | (2006.01) |
| *A61K 31/7004* | (2006.01) |
| *A61K 31/714* | (2006.01) |
| *A61K 33/06* | (2006.01) |
| *A61K 33/20* | (2006.01) |
| *A61K 33/30* | (2006.01) |
| *A23L 33/15* | (2016.01) |

(52) U.S. Cl.
CPC ............ *A61K 9/0019* (2013.01); *A23L 33/15* (2016.08); *A61K 31/197* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/7004* (2013.01); *A61K 31/714* (2013.01); *A61K 33/06* (2013.01); *A61K 33/20* (2013.01); *A61K 33/30* (2013.01)

(58) Field of Classification Search
None
See application file for complete search history.

(56) References Cited

U.S. PATENT DOCUMENTS

2006/0211631 A1* 9/2006 Mitsumoto .......... A61K 31/401
514/23
2010/0143498 A1* 6/2010 Shigeta ................ A61K 9/0019
424/643

FOREIGN PATENT DOCUMENTS

| EP | 0 704 199 A1 | 4/1996 |
|---|---|---|
| EP | 0 747 033 A1 | 12/1996 |
| EP | 2 567 700 A1 | 3/2013 |
| JP | 10-203959 | 8/1998 |
| JP | 11-158061 | 6/1999 |
| JP | 2001-55328 | 2/2001 |
| JP | 2003-55195 | 2/2003 |
| JP | 2003-171312 A | 6/2003 |
| JP | 2004-001900 * | 1/2004 |
| JP | 2004-1900 | 1/2004 |
| JP | 2006-124287 * | 5/2006 |
| JP | 2006-137745 * | 6/2006 |
| JP | 5752682 B2 | 5/2015 |
| WO | WO 2010/047302 A1 | 4/2010 |

OTHER PUBLICATIONS

Translation of Kikuchi et al (JP 2006137745). Publication date of foreign patent document Jun. 1, 2006.*
Translation of Muraoka et al (JP 2004001900). Publication date of forein patent document Jan. 8, 2004.*
International Search Report dated Jun. 14, 2011 in Application No. PCT/JP2011/060899 (With English Translation).
Document attached to drug for medical use, Fulcaliq (registered trademark), revised in Oct. 2009, 19 pages (With English Translation).
Document attached to drug for medical use, Neoparen (registered trademark), revised in Jul. 2009, 25 pages (With English Translation).
Takuro Nakamura, et al., "Regarding blood vitamin $B_1$ concentration of emergency patient under treatment with peripheral venous nutrition", Surgery and metabolism/nutrition, vol. 36, No. 6, 2002, 18 pages (With English Translation).

(Continued)

*Primary Examiner* — Allison Fox
(74) *Attorney, Agent, or Firm* — Oblon, McClelland, Maier & Neustadt, L.L.P.

(57) ABSTRACT

A nutrition infusion is provided for administration through a peripheral vein that contains a vitamin B group and vitamin C stably and includes two solutions of a sugar solution and an amino acid solution. In the nutrition infusion for administration through a peripheral vein, the sugar solution contains vitamin B1, vitamin B12, and pantothenic acid and has a pH of 4.7 to 5.5, and the amino acid solution contains vitamin B2, folic acid, vitamin C, and biotin and has a pH of 7.0 to 7.5.

26 Claims, No Drawings

(56) References Cited

OTHER PUBLICATIONS

Document attached to drug for medical use, Paresafe (registered trademark), revised in Apr. 2010, 14 pages (With English Translation).
Document attached to drug for medical use, Amigrand (registered trademark), revised in Oct. 2009, 18 pages (With English Translation).
Document attached to drug for medical use, Bfluid (registered trademark), revised in Jul. 2009, 21 pages (With English Translation).
Extended European Search Report issued Aug. 27, 2013 in Patent Application No. 11777492.7.
Japanese Office Action dated Sep. 20, 2016 in Patent Application No. 2015-101841(with English translation).
Notification (Information Statement), dated Aug. 8, 2017, in Japanese Patent Application No. 2016-206232 (with English Translation).
Hajime Matsubara et al., "Stability of Vitamin B1 and C in New Total Parenteral Nutrition Kit Products in Presence of Trace Elements", Japanese Journal of Pharmaceutical Health Care and Sciences, vol. 36, No. 1, pp. 10 to 17 and the last page, Issued: Jan. 10, 2010.
Ingredient table of Elneopa No. 1 and Elneopa No. 2 Injections, revised in Nov. 2015.
Ingredient table of Neoparen No. 1 and Neoparen No. 2 Injections, revised in Jan. 2012.

\* cited by examiner

VITAMIN-CONTAINING NUTRITION INFUSION FOR ADMINISTRATION THROUGH PERIPHERAL VEIN

TECHNICAL FIELD

The present invention relates to a nutrition infusion for administration through a peripheral vein, which includes two solutions of a sugar solution and an amino acid solution containing a vitamin B group and vitamin C.

BACKGROUND ART

In order to supply nutrients vital for sustaining life, such as carbohydrates, amino acids, and electrolytes, to a patient who cannot be supplied with nutrients orally or is insufficiently supplied with nutrients orally, intravenous nutrition therapy in which an infusion is administered through a vein is widely performed. The intravenous nutrition therapy is roughly classified into central venous nutrition therapy and peripheral venous nutrition therapy, by the route of administration.

In the central venous nutrition therapy, an infusion high in calories is administered through the central vein for a relatively long time. Accordingly, it is necessary to appropriately add vitamins and trace elements that could become deficient during the period of administration. In clinical practice, vitamin formulations and trace element formulations are added at the time of use by being mixed in the infusion. However, the mixing operation is cumbersome, and there is a concern that bacterial contamination or ingress of foreign substances will be caused by the mixing operation, which may be a cause of medical malpractice. Therefore, regarding a high-calorie infusion for administration through a central vein that is used for a long time, a formulation which contains reducing sugar, amino acids, electrolytes, and vitamins and in which solutions can be mixed in a sterile state is under development and has been commercialized. For example, PTLs 1 and 2 and NPLs 1 and 2 disclose an infusion formulation for central venous nutrition that is mixed with vitamins.

On the other hand, in the peripheral venous nutrition therapy, a nutrition infusion containing about 30% to 60% of the calories administered by the central venous nutrition therapy is administered through the peripheral vein. Duration of administration thereof is relatively short, such as 3 days to 2 weeks, and initially, mixing of vitamins was not particularly considered for the peripheral venous nutrition therapy. However, it is reported that the vitamin B1 concentration is reduced during the peripheral venous nutrition therapy (NPL 3). Vitamin B1 deficiency is highly likely to cause serious side-effects such as lactic acidosis, and accordingly, in order to improve safety, a nutrition infusion formulation for peripheral vein administration mixed with vitamin B1 in advance is reported (PTL 3). In addition, several formulations have been commercialized (NPLs 4, 5, and 6).

In recent years, it has been a reported that deficiency of vitamins other than vitamin B1 can be potentially caused in patients receiving infusion through a peripheral vein, and that it should be considered that the infusion for a peripheral vein should also be mixed with plural vitamins that are particularly necessary for the metabolism of sugar and amino acids (PTL 4).

However, each of the components including reducing sugar, amino acids, electrolytes, and vitamins shows sufficient stability or solubility in different pH regions. On the other hand, regarding the nutrition infusion for administration through a peripheral vein, if the pH of infusion is acidic at the time of administration, phlebitis or angialgia is easily caused, so it is desired that the pH be neutral. In addition, some of the respective components interact with each other. Therefore, in consideration of this point, a stable nutrition infusion for administration through a peripheral vein mixed in advance with vitamins is desired.

For example, folic acid causes turbidity in the acidic region of a sugar electrolyte solution, and even when mixed with an amino acid solution, folic acid causes incompatibility if vitamin B2, vitamin C, and the like coexist, so it is difficult to obtain a stable formulation. Therefore, for the infusion for administration through a central vein mixed with vitamins, which is used for the central venous nutrition therapy, a third chamber separated from the sugar electrolyte or amino acid solution is provided to separate the folic acid from the sugar electrolyte solution or vitamins B2 and C, so as to stabilize the infusion (PTL 2, NPLs 1 and 2). In addition, there is a disclosure regarding a method of mixing vitamins with an infusion for administration through a central vein that includes two solutions of a sugar solution and an amino acid solution. However, in this infusion, pH of the sugar solution and amino acid solution is 3.5 to 4.5 and 5.0 to 7.0, respectively, so the pH of the both solutions is acidic (PTLs 5 and 6). Moreover, regarding a nutrition infusion for administration through a peripheral vein, PTL 4 discloses an infusion for administration through a peripheral vein that is mixed with a vitamin B group, which is obtained by mixing vitamin B12 in an amino acid solution not containing sulfite, and mixing vitamin B1 in a sugar solution. However, PTL 4 discloses that since vitamin C, biotin, pantothenic acid, and the like sometimes decompose other vitamin B groups, it is preferable to add those components immediately before the administration.

CITATION LIST

Patent Literature

[PTL 1] Japanese Unexamined Patent Application, First Publication No. H11-158061

[PTL 2] Japanese Unexamined Patent Application, First Publication No. 2001-55328

[PTL 3] Japanese Unexamined Patent Application, First Publication No. 2003-55195

[PTL 4] Japanese Unexamined Patent Application, First Publication No. 2006-137745

[PTL 5] Japanese Unexamined Patent Application, First Publication No. H10-203959

[PTL 6] Japanese Unexamined Patent Application, First Publication No. 2004-1900

[NPL 1] Document attached to drug for medical use, Fulcaliq (registered trademark), revised in October, 2009

[NPL 2] Document attached to drug for medical use, Neoparen (registered trademark), revised in July, 2009

[NPL 3] Nakamura et al., "Regarding blood vitamin B1 concentration of emergency patient under treatment with peripheral venous nutrition", Surgery and metabolism/nutrition, 36 (6), p307 (2002)

[NPL 4] Document attached to drug for medical use, Paresafe (registered trademark), revised in April, 2010

[NPL 5] Document attached to drug for medical use, Amigrand (registered trademark), revised in October, 2009

[NPL 6] Document attached to drug for medical use, Bfluid (registered trademark), revised in July, 2009

SUMMARY OF INVENTION

Technical Problem

The present invention provides a nutrition infusion for administration through a peripheral vein that contains reducing sugar, amino acids, and electrolytes and further stably contains a vitamin B group and vitamin C.

Solution to Problem

In order to solve the above problem, the present inventors conducted a thorough examination. As a result, they found that in a nutrition infusion for administration through a peripheral vein that includes two solutions of a sugar solution and an amino acid solution, by sorting respective vitamins into the two solutions and adjusting pH of each of the two solutions to be in a specific range, the respective vitamins can be held stably for a long time, and even when the sugar solution is mixed with the amino acid solution at the time of use, a decrease in the content of active ingredients becomes small, thereby completing the present invention.

That is, the present invention provides a nutrition infusion for administration through a peripheral vein according to the following (1) to (8).

(1) A nutrition infusion for administration through a peripheral vein that includes two solutions of a sugar solution containing reducing sugar and an amino acid solution containing amino acids, wherein the sugar solution further contains vitamin B1, vitamin B12, and pantothenic acids and has a pH of 4.7 to 5.5, and the amino acid solution further contains vitamin B2, folic acid, vitamin C, and biotin and has a pH of 7.0 to 7.5.

(2) The nutrition infusion for administration through a peripheral vein, wherein the reducing sugar is glucose, and a glucose concentration in the infusion obtained after the sugar solution is mixed with the amino acid solution is 4 w/v % to 10 w/v %.

(3) The nutrition infusion for administration through a peripheral vein, wherein the amino acid solution further contains sulfite in an amount of 25 mg/L to 100 mg/L.

(4) The nutrition infusion for administration through a peripheral vein, wherein the sugar solution further contains vitamin B6, and the amino acid solution further contains a nicotinic acid derivative.

(5) The nutrition infusion for administration through a peripheral vein, wherein the sugar solution contains acetic acid as a pH adjustor, and the amino acid solution contains citric acid as a pH adjustor.

(6) The nutrition infusion for administration through a peripheral vein according to (5), wherein a mixed solution obtained by mixing the sugar solution with the amino acid solution has a pH of 6.5 to 7.4, and a citric acid concentration in the mixed solution is 5 mEq/L to 15 mEq/L.

(7) The nutrition infusion for administration through a peripheral vein, wherein in the infusion obtained after the sugar solution is mixed with the amino acid solution, water-soluble vitamin components are mixed in the following compositional range:
Vitamin B1 at 1 mg/L to 10 mg/L,
Vitamin B2 at 1 mg/L to 5 mg/L converted in terms of riboflavin,
Vitamin B6 at 1 mg/L to 5 mg/L,
Vitamin B12 at 1 μg/L to 10 μg/L,
Pantothenic acids at 4 mg/L to 16 mg/L,
Nicotinic acid derivative at 10 mg/L to 40 mg/L,
Folic acid at 100 μg/L to 400 μg/L,
Biotin at 25 μg/L to 100 μg/L, and
Vitamin C at 50 mg/L to 200 mg/L.

(8) The nutrition infusion for administration through a peripheral vein, wherein the sugar solution further contains sodium chloride in an amount of 0.5 g/L to 2 g/L, a calcium chloride hydrate in an amount of 0.2 g/L to 1 g/L, sodium lactate in an amount of 2 g/L to 15 g/L, a magnesium sulfate hydrate in an amount of 0.5 g/L to 2 g/L, and a zinc sulfate hydrate in an amount of 1 mg/L to 4 mg/L, the amino acid solution contains amino acids in an amount of 50 g/L to 300 g/L converted in terms of free amino acids, and a volume ratio between the sugar solution and the amino acid solution is 2:1 to 3:1.

The present invention also provides nutrition therapy including administering the infusion for administration through a peripheral vein according to (1) to (8) through a peripheral vein to a patient insufficiently supplied with nutrients orally.

The present invention also provides the infusion for administration through a peripheral vein according to (1) to (8), which is for administering nutrients through a peripheral vein to a patient insufficiently supplied with nutrients orally.

Advantageous Effects of Invention

The nutrition infusion for administration through a peripheral vein of the present invention contains reducing sugar, amino acids, electrolytes, a vitamin B group, and vitamin C stably, has a pH that is in a range appropriate for administration through a peripheral vein at the time of use, and makes it possible to simply and safely supply nutrients with less concern for deficiency of vitamins.

DESCRIPTION OF EMBODIMENTS

Hereinafter, the nutrition infusion for administration through a peripheral vein of the present invention (also referred to as an "infusion formulation of the present invention" below in some cases) will be described in detail.

The sugar solution in the infusion formulation of the present invention contains reducing sugar as a basic composition and preferably does not contain sulfite and a salt thereof. Usable reducing sugar is not particularly limited as long as it is reducing sugar generally used in an infusion formulation. Examples thereof include glucose, fructose, and maltose, but in view of bioavailability, glucose is particularly preferable. The concentration of reducing sugar in the infusion obtained after the sugar solution is mixed with the amino acid solution is preferably 4 w/v % to 10 w/v %, and particularly preferably 7 w/v % to 8 w/v %. When the concentration is 4 w/v % or less, catabolism is caused easily. When the concentration exceeds 10 w/v %, this is not preferable since the osmotic pressure of the infusion increases causing possible phlebitis or angialgia.

The sugar solution is mixed with vitamin B1, vitamin B12, and pantothenic acids. These vitamins may be mixed in as they are or in the form of a salt or a derivative thereof. Vitamin B1 includes, for example, thiamine, thiamine disulfide, fursultiamine, benfotiamine, a salt of these, and the like, and thiamine chloride hydrochloride is particularly preferable; vitamin B12 includes, for example, cyanocobalamin and a salt thereof, and cyanocobalamin is particularly preferable; pantothenic acids include, for example, pantothenic acid or a calcium salt thereof, panthenol, and the like, and panthenol is preferable.

In addition, the sugar solution is preferably further mixed with vitamin B6, and at this time, vitamin B6 may be used as is or in the form of a salt or a derivative thereof. Examples of vitamin B6 include pyridoxine, pyridoxal, pyridoxamine, and a salt of these, and pyridoxine hydrochloride is preferable.

The pH of the sugar solution is adjusted to 4.7 to 5.5 and more preferably 4.9 to 5.5. The pH can be adjusted appropriately using a generally used organic acid, inorganic acid, organic base, and inorganic base as a pH adjustor, but in order to enhance the stability of vitamin B1, it is particularly preferable to use acetic acid. In a pH range of from 4.7 to 5.5, dissolved oxygen remaining in the sugar solution does not easily exert influence during the preparation of the infusion, so it is possible to inhibit the decrease in the content of various vitamins including vitamin B1 caused when high-pressure steam sterilization or heat sterilization is performed. Accordingly, it is possible to stably prepare the infusion without strictly controlling the amount of the dissolved oxygen or the oxygen remaining in the inner space of a container. For example, even if about 4 ppm of dissolved oxygen is present in the sugar solution, it is possible to stably prepare the infusion.

Examples of amino acids mixed in the amino acid solution include amino acids (essential amino acids and nonessential amino acids) contained in the amino acid infusion having been used in the related art for the purpose of supplying nutrients to living organisms. Particularly, compositions rich in branched-chain amino acids (L-leucine, L-isoleucine, and L-valine) are preferable. These amino acids are generally used in the form of free amino acid. The free form is not particularly limited, and a pharmaceutically acceptable salt can also be used. In addition, a portion of the amino acids can also be used in the acylated form such as L-acetyl cysteine or in the form of a peptide such as alanyl glutamine. The total amount of amino acids contained in the infusion that is obtained after the sugar solution is mixed with amino acid solution is preferably 20 g/L to 40 g/L converted in terms of free amino acid, so as to inhibit catabolism and promote synthesis of proteins.

The preferable amount (converted in terms of free amino acid) of amino acids mixed in the infusion obtained after the sugar solution is mixed with amino acid solution is as follows:

L-Isoleucine in an amount of 0.2 g/L to 14.0 g/L, more preferably 1.0 g/L to 6.0 g/L, L-Leucine in an amount of 0.4 g/L to 20.0 g/L, more preferably 1.0 g/L to 10.0 g/L, L-Lysine in an amount of 0.2 g/L to 14.0 g/L, more preferably 1.0 g/L to 5.0 g/L, L-Methionine in an amount of 0.1 g/L to 8.0 g/L, more preferably 0.5 g/L to 5.0 g/L, L-Phenyl alanine in an amount of 0.2 g/L to 12.0 g/L, more preferably 1.0 g/L to 5.0 g/L, L-Threonine in an amount of 0.1 g/L to 8.0 g/L, more preferably 0.5 g/L to 4.0 g/L, L-Tryptophan in an amount of 0.04 g/L to 3.0 g/L, more preferably 0.2 g/L to 1.5 g/L, L-Valine in an amount of 0.1 g/L to 16.0 g/L, more preferably 1.0 g/L to 6.0 g/L, L-Alanine in an amount of 0.2 g/L to 14.0 g/L, more preferably 1.0 g/L to 6.0 g/L, L-Arginine in an amount of 0.2 g/L to 14.0 g/L, more preferably 1.0 g/L to 7.0 g/L, L-Aspartic acid in an amount of 0.01 g/L to 4.0 g/L, more preferably 0.1 g/L to 2.0 g/L, L-Glutamic acid in an amount of 0.01 g/L to 6.0 g/L, more preferably 0.1 g/L to 2.0 g/L, L-Histidine in an amount of 0.1 g/L to 8.0 g/L, more preferably 0.5 g/L to 5.0 g/L, L-Proline in an amount of 0.1 g/L to 10.0 g/L, more preferably 0.5 g/L to 5.0 g/L, L-Serine in an amount of 0.1 g/L to 6.0 g/L, more preferably 0.2 g/L to 3.0 g/L, L-Tyrosine in an amount of 0.01 g/L to 2.0 g/L, more preferably 0.05 g/L to 1.0 g/L, Glycine in an amount of 0.1 g/L to 12.0 g/L, more preferably 1.0 g/L to 5.0 g/L, and L-Cysteine in an amount of 0.01 g/L to 2.0 g/L, more preferably 0.1 g/L to 2.0 g/L The amino acid solution is mixed with vitamin B2, folic acid, vitamin C, and biotin as vitamins. These vitamins may also be used as they are or used in the form of a salt or a derivative thereof. Vitamin B2 includes, for example, riboflavin, riboflavin phosphoric acid esters and a sodium salt thereof, and flavin mononucleotide, and particularly, riboflavin sodium phosphate is preferable; as folic acid, folic acid itself is preferable; vitamin C includes, for example, ascorbic acid, sodium ascorbate, and the like, and ascorbic acid is particularly preferable; and as biotin, biotin itself is preferable.

In addition, the amino acid solution is preferably further mixed with a nicotinic acid derivative. Herein, the nicotinic acid derivative includes, for example, nicotinic acid, nicotinamide, a nicotinic acid sodium salt, and a nicotinic acid methyl ester, and nicotinamide is preferable.

The pH of the amino acid solution is adjusted to 7.0 to 7.5 and particularly preferably to 7.0 to 7.2. Moreover, the pH is preferably 7.1 to 7.5, and particularly preferably 7.1 to 7.2. If the pH is adjusted to 7.0 to 7.5, vitamin B2, vitamin C, and folic acid can be stably mixed in the amino acid solution, and biotin can also be stably mixed in. If the pH is less than 7, folic acid particularly becomes unstable, and if the pH exceeds 7.5, vitamin B2 becomes unstable. The pH adjustor for the amino acid solution is not particularly limited as long as it is physiologically acceptable. For example, an organic acid, an inorganic acid, an organic base, and an inorganic base can be used, and citric acid is particularly preferable. When citric acid is used, the citric acid concentration in the mixed solution obtained by mixing the sugar solution with the amino acid solution is set to preferably 5 mEq/L to 15 mEq/L and more preferably 10 mEq/L to 15 mEq/L. If the concentration exceeds 15 mEq/L, pH of the amino acid solution becomes less than 7, so the stability of vitamins such as folic acid deteriorates. If the concentration is less than 5 mEq/L, stability of vitamin C in the mixed solution obtained by mixing the sugar solution with the amino acid solution deteriorates.

It is preferable to add sulfite to the amino acid solution as a stabilizer. As the sulfite, sodium hydrogen sulfite is preferable, and the amount of sulfite added is 25 mg/L to 100 mg/L and preferably 25 mg/L to 70 mg/L in the amino acid solution. If the amount of sulfite is less than 25 mg/L, stability of oxidizable amino acids such as tryptophan or N-acetyl cysteine deteriorates during preparation and storage. If the amount is 100 mg/L or more, stability of folic acid mixed in the amino acid solution deteriorates. In addition, when the sugar solution is mixed with the amino acid solution, vitamin B1 is decomposed depending on the sulfite concentration, so the sulfite concentration is preferably set to 100 mg/L or less.

Electrolytes can be mixed with either the sugar solution or the amino acid solution. The electrolytes are not particularly limited as long as they are used for general electrolyte infusions and the like. Examples of the electrolytes include water-soluble salts providing ions such as a sodium ion ($Na^+$), a chloride ion ($Cl^-$), a magnesium ion ($Ma^{2+}$), a potassium ion ($K^+$), a calcium ion ($Ca^{2+}$), a phosphoric acid ion (more specifically, a hydrogen phosphate ion ($HPO_4^{2-}$) or a dihydrogen phosphate ion ($H_2PO_4^-$)), and a zinc ion ($Zn^{2+}$).

Examples of the water-soluble salts providing a sodium ion include sodium chloride, sodium acetate, sodium citrate, sodium lactate, sodium dihydrogen phosphate, disodium hydrogen phosphate, sodium glycerophosphate, sodium sulfate, sodium bicarbonate, and the like, and among these, sodium chloride, sodium bicarbonate, and sodium citrate are preferable.

Examples of the water-soluble salts providing a chloride ion include sodium chloride, potassium chloride, calcium chloride, magnesium chloride, and the like.

Examples of the water-soluble salts providing a magnesium ion include magnesium sulfate, magnesium chloride, magnesium acetate, and the like, and among these, magnesium chloride is preferable.

Examples of the water-soluble salts providing a potassium ion include potassium chloride, potassium iodide, potassium acetate, potassium citrate, potassium dihydrogen phosphate, dipotassium hydrogen phosphate, potassium glycerophosphate, potassium sulfate, potassium lactate, and the like, and among these, potassium chloride is preferable.

Examples of the water-soluble salts providing a calcium ion include calcium chloride, calcium gluconate, calcium pantothenate, calcium lactate, calcium acetate, and the like, and among these, calcium chloride is preferable.

Examples of the water-soluble salts providing a phosphoric acid ion include sodium dihydrogen phosphate, disodium hydrogen phosphate, magnesium hydrogen phosphate, magnesium dihydrogen phosphate, potassium dihydrogen phosphate, potassium hydrogen phosphate, calcium hydrogen phosphate, calcium dihydrogen phosphate, and the like.

Examples of the water-soluble salts providing a zinc ion include zinc sulfate and the like.

In addition, as the electrolytes contained in the infusion formulation of the present invention, compositions in the form of a hydrate and the like can also be used.

The mixed solution obtained after the sugar solution is mixed with the amino acid solution is administered through a peripheral vein. In order to prevent angialgia or phlebitis, the pH of the mixed solution is preferably neutral, more specifically, is 6.5 to 7.4. Likewise, in order to prevent angialgia or phlebitis, titratable acidity thereof is preferably set to 10 or less. In the infusion formulation of the present invention, the pH of the sugar solution ranges from 4.7 to 5.5, and the pH of amino acid solution ranges from 7.0 to 7.5, and the stability of vitamins contained in the sugar solution and amino acid solution is compatible with the pH (6.5 to 7.4) of the mixed solution.

A volume ratio between the sugar solution and the amino acid solution is preferably 1:2 to 1:3 in terms of the amino acid solution:sugar solution. Here, the sugar solution preferably further contains sodium chloride at a concentration of 0.5 g/L to 2 g/L, a calcium chloride hydrate at a concentration of 0.2 g/L to 1 g/L, sodium lactate at a concentration of 2 g/L to 15 g/L of, a magnesium sulfate hydrate at a concentration of 0.5 g/L to 2 g/L, and a zinc sulfate hydrate at a concentration of 1 mg/L to 4 mg/L, and the amino acid solution preferably contains amino acids at a concentration of 50 g/L to 300 g/L converted in terms of free amino acids.

In the infusion formulation of the present invention, the respective concentrations of the water-soluble vitamin components in the mixed solution obtained after the sugar solution is mixed with the amino acid solution are preferably as follows:

Vitamin B1 at 1 mg/L to 10 mg/L,
Vitamin B2 at 1 mg/L to 5 mg/L converted in terms of riboflavin,
Vitamin B6 at 1 mg/L to 5 mg/L
Vitamin B12 at 1 µg/L to 10 µg/L
Pantothenic acids at 4 mg/L to 16 mg/L,
Nicotinic acid derivative at 10 mg/L to 40 mg/L,
Folic acid at 100 µg/L to 400 µg/L
Biotin at 25 µg/L to 100 µg/L, and
Vitamin C at 50 mg/L to 200 mg/L.

It is preferable that the components in the mixed solution obtained by mixing the sugar solution with the amino acid solution remain stable for at least 24 hours after the mixing, excluding the stabilizer. Specifically, compared to the content immediately after mixing, the content after 24 hours is decreased by preferably 10% or less and particularly preferably 5% or less. In this case, decrease in the vitamin content during administration is inhibited, so it is possible to reduce the risk that a patient may suffer from vitamin deficiency.

A multi-chamber container in which respective chambers containing the sugar solution and the amino acid solution are separated from each other by communicable partitions, which is a container for containing the infusion formulation of the present invention, is not particularly limited, and for example, known containers can be used. As the material of the container, for example, polyethylene, polypropylene, cyclic polyolefin, and the like are preferable, and these can be optionally formed into a multi-layered film. Among these, an infusion bag of which the partition is constituted with an easy-peel seal is preferable since this makes it easy to cause the partitions to communicate with each other during administration.

The sugar solution and the amino acid solution can be filled in the container according to common methods. The space of the respective chambers is preferably substituted with nitrogen gas, but a strict substitution rate such as a substitution rate of 100% is not necessarily required.

The container filled with the medicinal solutions is sterilized by heating under a nitrogen atmosphere according to common methods. After sterilization, the container is packed by being sealed in an outer packing material made of a gas-nonpermeable multi-layered film having light-shielding properties together with a deoxidant.

EXAMPLE

Next, the present invention will be described in more detail with reference to examples, but the present invention is not limited thereto.

Example 1

According to the amounts described in Table 1, glucose and electrolytes were dissolved in water for injection, and then thiamine hydrochloride, pyridoxine hydrochloride, cyanocobalamin, and panthenol were dissolved in the solution. The pH thereof was adjusted to 5.1 by using acetic acid, and then the total amount thereof was adjusted to 350 mL, followed by filtration by using a membrane filter (0.2 μm), thereby preparing a sugar solution.

One of the chambers of a multi-chamber container made of polyethylene that was divided by partitions was filled with 350 mL of the sugar solution and sealed. Nitrogen bubbling of the medicinal solution and nitrogen substitution for the space of the container were not performed. The content of dissolved oxygen in the medicinal solution measured after filling and sealing was about 4 ppm. According to a common method, the container filled with the solution was sterilized by high-pressure steam under nitrogen substitution, and then sealed in an outer packing material made of a gas-nonpermeable film having light-shielding properties together with a deoxidant (Ageless, manufactured by MITSUBISHI GAS CHEMICAL COMPANY, INC.), thereby obtaining an infusion formulation.

TABLE 1

| | Component | |
|---|---|---|
| Sugar solution | Glucose | 37.5 g |
| | Sodium chloride | 0.252 g |
| | Calcium chloride hydrate | 0.184 g |
| | Magnesium sulfate hydrate | 0.312 g |
| | Sodium L-lactate (50%) | 2.852 g |
| | Zinc sulfate hydrate | 0.7 mg |
| | Thiamine hydrochloride (B1) | 1.9 mg |
| | Pyridoxine hydrochloride (B6) | 1.25 mg |
| | Cyanocobalamin (B12) | 2.5 μg |
| | Panthenol | 3.75 mg |
| | Total amount | 350 mL |

Comparative Example 1

An infusion formulation was obtained in the same manner as in Example 1, except that the pH was adjusted to 4.5 by using acetic acid as a pH adjustor.

Test Example 1

Setting pH of Sugar Solution

The infusion formulations prepared in Example 1 and Comparative Example 1 were stored for 2 weeks and 1 month under conditions of 25° C. and 60% RH, and then the thiamine content was measured by liquid chromatography. The results are shown in Table 2, and the content is expressed as a percentage based on the mixed amount. In Example 1, vitamin B1 was shown to be stable. On the other hand, in Comparative Example 1, the vitamin B1 content was decreased greatly.

TABLE 2

| | pH | After sterilization | Storage for 2 weeks | Storage for 1 month |
|---|---|---|---|---|
| Example 1 | 5.1 | 90.8% | 91.7% | 90.7% |
| Comparative Example 1 | 4.5 | 91.4% | 82.4% | 81.2% |

Example 2

According to the amount described in Table 1, glucose and electrolytes were dissolved in water for injection, and then thiamine hydrochloride, pyridoxine hydrochloride, cyanocobalamin, and panthenol were dissolved in the solution. The pH thereof was adjusted to 5.1 by using acetic acid, and then the total amount thereof was adjusted to 350 mL, followed by filtration by using a membrane filter (0.2 μm), thereby preparing a sugar solution.

One of the chambers of a multi-chamber container made of polyethylene that was divided by partitions was filled with 350 mL of the sugar solution and sealed, and the space of chamber was substituted with nitrogen, followed by sealing. The content of dissolved oxygen in the medicinal solution measured after filling and sealing was about 4 ppm. According to a common method, the container filled with the solution was sterilized by high-pressure steam under nitrogen substitution, and then sealed in an outer packing material made of a gas-nonpermeable film having light-shielding properties together with a deoxidant (Ageless, manufactured by MITSUBISHI GAS CHEMICAL COMPANY, INC.), thereby obtaining an infusion formulation.

Examples 3, 3-2, and 3-3

Infusion formulations were prepared in the same manner as in Example 2, except that the pH thereof was adjusted to a set value by using the pH adjustor shown in Table 3, thereby obtaining Examples 3, 3-2, and 3-3.

TABLE 3

| | pH adjuster | Set pH |
|---|---|---|
| Example 3 | Acetic acid | 4.8 |
| Example 3-2 | Citric acid | 5.1 |
| Example 3-3 | Citric acid | 4.8 |

Test Example 2

Setting pH Adjustor of Sugar Solution

The infusion formulations prepared in the above respective Examples 2, 3, 3-2, and 3-3 were stored for 1 month under conditions of 40° C. and 75% RH, and then the vitamin B1 content, vitamin B6 content, and vitamin B12 content were measured by liquid chromatography. The results are shown in Table 4. In addition, the content is expressed as a percentage based on the mixed amount. It was confirmed that when citric acid was used as a pH adjustor, the content of vitamin B1 and B12 tended to be decreased compared to a case where acetic acid was used. This tendency was marked when pH was 5.1.

TABLE 4

| | pH | pH adjuster | Vitamin B1 | Vitamin B6 | Vitamin B12 |
|---|---|---|---|---|---|
| Example 2 | 5.1 | Acetic acid | 89.7% | 96.0% | 92.7% |
| Example 3 | 4.8 | Acetic acid | 87.9% | 95.2% | 91.5% |
| Example 3-2 | 5.1 | Citric acid | 85.1% | 95.2% | 87.3% |
| Example 3-3 | 4.8 | Citric acid | 86.5% | 96.8% | 88.2% |

Example 4

According to the amount described in Table 5, the respective amino acids were dissolved in water for injection, and then riboflavin sodium phosphate, ascorbic acid, folic acid, biotin, and nicotinamide were dissolved in the solution. As a stabilizer, sodium hydrogen sulfite was dissolved in the solution. The pH thereof was adjusted to 7.2 by using citric acid, and then water was added thereto to adjust the total amount thereof to 150 mL, followed by filtration by using a membrane filter (0.2 μm), thereby preparing an amino acid solution.

One of the chambers of a multi-chamber container made of polyethylene that was divided by partitions was filled with 150 mL of the amino acid solution under nitrogen substitution and sealed. According to a common method, the container filled with the solution was sterilized by high-pressure steam under a nitrogen atmosphere, and then sealed in an outer packing material made of a gas-nonpermeable film having light-shielding properties together with a deoxidant (Ageless, manufactured by MITSUBISHI GAS CHEMICAL COMPANY, INC.), thereby obtaining an infusion formulation.

TABLE 5

| Component | | |
|---|---|---|
| Amino acid solution | L-Arginine | 1.575 g |
| | L-Tyrosine | 0.075 g |
| | L-Isoleucine | 1.200 g |
| | L-Leucine | 2.100 g |
| | L-Methionine | 0.585 g |
| | L-Valine | 1.200 g |
| | L-Lysine hydrochloride | 1.965 g |
| | L-Threonine | 0.855 g |
| | L-Alanine | 1.200 g |
| | L-Aspartic acid | 0.150 g |
| | L-Glutamic acid | 0.150 g |
| | L-Proline | 0.750 g |
| | L-Serine | 0.450 g |
| | Glycine | 0.885 g |
| | L-Phenyl alanine | 1.050 g |
| | L-Histidine | 0.750 g |
| | L-Tryptophan | 0.300 g |
| | L-Acetyl cysteine | 0.202 g |
| | Sodium hydrogen sulfite | 7.5 mg |
| | Riboflavin sodium phosphate (B2) | 1.25 mg |
| | Ascorbic acid (C) | 50.0 mg |
| | Folic acid (F) | 100 μg |
| | Biotin (H) | 25 μg |
| | Nicotinamide (NA) | 10 mg |
| | Total amount | 150 mL |

Example 5 and Comparative Examples 2 and 3

Infusion formulations were prepared in the same manner as in Example 4, except that the pH was adjusted to the value shown in Table 6 by using citric acid, thereby obtaining Example 5 and Comparative Examples 2 and 3.

TABLE 6

| | Adjusted pH |
|---|---|
| Example 5 | 7.0 |
| Comparative Example 2 | 6.8 |
| Comparative Example 3 | 6.5 |

Test Example 3

Setting pH of Amino Acid Solution

The infusion formulations prepared in Examples 4 and 5 and Comparative Examples 2 and 3 were stored for 12 months at 60° C. and 60% RH, and the content of folic acid and vitamin B2 was measured after the infusion formulations were stored for 6 months and 12 months. The results are shown in Table 7. In addition, the content is expressed as a percentage based on the mixed amount. It was confirmed that the content was stable in Examples 4 and 5 having a pH equal to or more than 7.0 even after a long period of storage. On the other hand, the content of folic acid was decreased greatly in Comparative Examples 2 and 3, which was marked at a pH of 6.5.

TABLE 7

| | | Folic acid | | Vitamin B2 | |
|---|---|---|---|---|---|
| | pH | 6 months | 12 months | 6 months | 12 months |
| Example 4 | 7.2 | 96.7% | 93.5% | 91.8% | 90.6% |
| Example 5 | 7.0 | 97.7% | 89.9% | 92.8% | 91.8% |
| Comparative Example 2 | 6.8 | 94.3% | 85.5% | 95.3% | 93.1% |
| Comparative Example 3 | 6.5 | 87.6% | 74.0% | 95.3% | 94.1% |

Examples 6 and 7 and Comparative Example 7-2

Infusion formulations were prepared in the same manner as in Example 4, except that sodium hydrogen sulfite was mixed in the amount shown in Table 8, thereby obtaining Examples 6 and 7 and Comparative Example 6.

TABLE 8

| | Amount of sodium hydrogen sulfite mixed |
|---|---|
| Example 6 | 3.75 mg |
| Example 7 | 15 mg |
| Example 7-2 | 30 mg |

Test Example 4

Setting Amount of Sodium Hydrogen Sulfite

The infusion formulations prepared in Examples 4, 6, 7, and 7-2 were stored for 21 days at 60° C., and then the residual rate of folic acid and N-acetyl cysteine (NAC) was measured. The results are shown in Table 9. The content is expressed as a percentage based on the mixed amount. Compared to Examples 4, 6, and 7, Example 7-2 in which the concentration of sodium hydrogen sulfite was high showed a large degree of decrease in the folic acid content. In addition, NAC showed high stability even at a concentration of sodium hydrogen sulfite of 25 mg/L.

TABLE 9

| | Concentration of sodium hydrogen sulfite | Folic acid | NAC |
|---|---|---|---|
| Example 6 | 25 mg/L | 90.7% | 94.3% |
| Example 4 | 100 mg/L | 88.4% | 95.1% |
| Example 7 | 100 mg/L | 83.2% | 95.8% |
| Example 7-2 | 200 mg/L | 72.9% | 95.4% |

Example 8

According to the amount described in Table 1, glucose and electrolytes were dissolved in water for injection, and thiamine hydrochloride, pyridoxine hydrochloride, cyanocobalamin, and panthenol were dissolved in the solution.

The pH thereof was adjusted to 5.1 by using acetic acid, and then the total amount thereof was adjusted to 350 mL, followed by filtration by using a membrane filter (0.2 μm), thereby preparing a sugar solution.

In addition, according to the amount described in Table 5, the respective amino acids were dissolved in water for injection, and then riboflavin sodium phosphate, ascorbic acid, folic acid, biotin, and nicotinamide were dissolved in the solution. Sodium hydrogen sulfite was dissolved in the solution as a stabilizer. 0.175 g of a citric acid monohydrate was added thereto, and then the pH thereof was adjusted to 7.0 by using acetic acid. Thereafter, the total amount thereof was adjusted to 150 mL, followed by filtration by using a membrane filter (0.2 μm), thereby obtaining an amino acid solution.

The above sugar solution and amino acid solution were filled to amounts of 350 mL and 150 mL, respectively, in each chamber of a multi-chamber container made of polyethylene that was divided by communicable partitions, and the space of the chamber was substituted with nitrogen, followed by sealing. The content of dissolved oxygen content in the sugar solution measured after filling and sealing was about 0.4 ppm. According to a common method, the container filled with the solutions was sterilized by high-pressure steam under a nitrogen environment, and then sealed in an outer packing material made of a gas-nonpermeable film having light-shielding properties together with a deoxidant (Ageless, manufactured by MITSUBISHI GAS CHEMICAL COMPANY, INC.), thereby obtaining the infusion formulation of the present invention. The pH measured when the sugar solution was mixed with the amino acid solution was 6.8.

Examples 9, 10, and 10-2

Infusion formulations were prepared in the same manner as in Example 8, except that a citric acid monohydrate was added to the amino acid solution according to the amount described in Table 10, and that the pH thereof was adjusted to 7.0 by using the pH adjustor described in the table, thereby obtaining Examples 9, 10, and 10-2. The pH measured when the sugar solution and amino acid solution of these infusion formulations were mixed with each other was 6.8.

TABLE 10

| | Amount of citric acid monohydrate added | pH adjuster | Adjusted pH |
|---|---|---|---|
| Example 9 | 0.35 g | Acetic acid | pH 7.0 |
| Example 10 | 0.53 g | 1N NaOH solution | pH 7.0 |
| Example 10-2 | 0.0 g | Acetic acid | pH 7.0 |

Test Example 5

Setting pH Adjustor of Amino Acid Solution

Regarding the infusion formulations prepared in Examples 8 to 10 and 10-2, the partition portions were opened to thoroughly mix the sugar solution with the amino acid solution at room temperature, and then the mixed solution was sampled after 0 hours, 12 hours, and 24 hours to measure the vitamin C content by titration. In addition, the mixed solution was stored in a light-shielded environment. The results are shown in Table 11. The value measured immediately after mixing was taken as 100%, and the content at each point in time of measurement is expressed as a percentage. In Examples 8 to 10, the vitamin C content measured 24 hours after mixing was 90% or more.

TABLE 11

| | Citric acid concentration in mixed solution | 12 hours after mixing | 24 hours after mixing |
|---|---|---|---|
| Example 10-2 | 0 mEq/L | 95.0% | 86.9% |
| Example 8 | 5 mEq/L | 95.5% | 91.0% |
| Example 9 | 10 mEq/L | 95.0% | 92.3% |
| Example 10 | 15 mEq/L | 98.0% | 95.5% |

Example 11

According to the amount described in Table 1, glucose and electrolytes were dissolved in water for injection, and then thiamine hydrochloride, pyridoxine hydrochloride, cyanocobalamin, and panthenol were dissolved in the solution. The pH thereof was adjusted to 5.1 by using acetic acid, and the total amount thereof was adjusted to 350 mL, followed by filtration by using a membrane filter (0.2 μm), thereby preparing a sugar solution.

In addition, according to the amount described in Table 5, the respective amino acids were dissolved in water for injection, and then riboflavin sodium phosphate, ascorbic acid, folic acid, biotin, and nicotinamide were dissolved in the solution. Sodium hydrogen sulfite was dissolved in the solution as a stabilizer. The pH thereof was adjusted to 7.2 by using citric acid. Thereafter, the total amount thereof was adjusted to 150 mL, followed by filtration by using a membrane filter (0.2 μm), thereby preparing an amino acid solution.

The above sugar solution and amino acid solution were filled to amounts of 350 mL and 150 mL respectively in each chamber of a multi-chamber container made of polyethylene that was divided by communicable partitions, and the space of the chamber was substituted with nitrogen, followed by sealing. The content of dissolved oxygen in the sugar solution measured after filling and sealing was about 0.4 ppm. According to a common method, high-pressure steam sterilization was performed under a nitrogen atmosphere, and then the resultant was sealed in an outer packing material made of a gas-nonpermeable film having light-shielding properties together with a deoxidant (Ageless, manufactured by MITSUBISHI GAS CHEMICAL COMPANY, INC.), thereby obtaining the infusion formulation of the present invention.

Test Example 6

Stability of Respective Vitamins

The infusion formulation prepared in Example 11 was stored for 3 months at 40° C. and 75% RH, and then the residual rate of the respective vitamins was measured. The results are shown in Table 12. In addition, the content is expressed as a percentage based on the mixed amount. From the results, it is considered that the infusion formulation of the present invention remains stable even when stored for a long time.

TABLE 12

| | Immediately after sterilization | Storage for 1 month | Storage for 3 months |
|---|---|---|---|
| Vitamin B1 | 93.3% | 90.6% | 83.5% |
| Vitamin B6 | 97.1% | 96.7% | 97.3% |
| Vitamin B12 | 86.3% | 89.7% | 91.2% |
| Panthenol | 97.8% | 97.6% | 96.8% |
| Vitamin B2 | 94.7% | 94.3% | 92.6% |
| Vitamin C | 96.1% | 97.6% | 99.7% |
| Folic acid | 95.8% | 96.5% | 89.7% |
| Biotin | 93.6% | — | 91.4% |
| Nicotinamide | 100.9% | 101.5% | 99.6% |

—: unmeasured

Test Example 7

Stability of Mixed Solution

Regarding the infusion formulations prepared in Example 11, the partition portions were opened to thoroughly mix the sugar solution with the amino acid solution at room temperature, and then the mixed solution was sampled after 0 hours, 24 hours, and 48 hours to measure the content of the respective vitamins and N-acetyl cysteine. In addition, the mixed solution was stored in a light-shielded environment. The results are shown in Table 13. The value measured immediately after mixing was taken as 100%, and the content at each point in time of measurement is expressed as a percentage. All of the respective components remained stable until 48 hours elapsed after mixing.

TABLE 13

| | After 24 hours | After 48 hours |
|---|---|---|
| Vitamin B1 | 99.4% | 94.1% |
| Vitamin B6 | 100.6% | 99.9% |
| Vitamin B12 | 96.0% | 97.9% |
| Panthenol | 100.0% | 100.2% |
| Vitamin B2 | — | 99.8% |
| Vitamin C | 97.1% | 92.2% |
| Folic acid | 96.4% | 96.2% |
| Biotin | 97.9% | 96.7% |
| Nicotinamide | 96.6% | 97.2% |
| N-acetyl cysteine | 98.3% | 97.5% |

Reference Example 1

37.5 g of glucose, 0.56 g of calcium gluconate, and 1.0 mg of thiamine hydrochloride were dissolved in water for injection. The pH thereof was adjusted to 5.5 by using acetic acid, and then water was added thereto to adjust the total amount thereof to 350 mL, followed by filtration by using a membrane filter (0.2 μm), thereby preparing a sugar solution.

One of the chambers of a multi-chamber container made of polyethylene that was divided by partitions was filled with 350 mL of the sugar solution and sealed. Nitrogen bubbling of the medicinal solution and nitrogen substitution for the space of the container were not performed. The content of dissolved oxygen in the medicinal solution measured after filling and sealing was about 4 ppm. According to a common method, the container filled with the solution was sterilized by high-pressure steam under nitrogen substitution, and then sealed in an outer packing material made of a gas-nonpermeable film having light-shielding properties together with a deoxidant (Ageless, manufactured by MITSUBISHI GAS CHEMICAL COMPANY, INC.), thereby obtaining an infusion formulation.

Reference Example 2

An infusion formulation was obtained in the same manner as in Reference Example 1, except that the pH thereof was adjusted to 5.0 by using acetic acid as a pH adjustor.

Reference Example 3

An infusion formulation was obtained in the same manner as in Reference Example 1, except that the pH thereof was adjusted to 4.5 by using acetic acid as a pH adjustor.

Reference Example 4

According to the amount described in Table 14, glucose and electrolytes were dissolved in water for injection, and then vitamin B1 (thiamine hydrochloride) was dissolved in the solution. The pH of the solution was adjusted to 5.3 by using acetic acid, and then water was added thereto to adjust the total amount thereof to 350 mL, followed by filtration by using a membrane filter (0.2 μm), thereby preparing a sugar solution.

One of the chambers of a multi-chamber container that was divided by partitions was filled with 350 mL of the sugar solution and sealed. Nitrogen bubbling of the medicinal solution and nitrogen substitution for the space of the container were not performed. The content of dissolved oxygen in the medicinal solution measured after filling and sealing was about 4 ppm. According to a common method, the container filled with the solution was sterilized by high-pressure steam under nitrogen substitution, and then sealed in an outer packing material made of a gas-nonpermeable film having light-shielding properties together with a deoxidant (Ageless, manufactured by MITSUBISHI GAS CHEMICAL COMPANY, INC.), thereby obtaining an infusion formulation.

TABLE 14

| | Component | |
|---|---|---|
| Sugar solution | Glucose | 37.5 g |
| | Sodium chloride | 0.399 g |
| | Calcium gluconate hydrate | 0.560 g |
| | Magnesium sulfate hydrate | 0.312 g |
| | Sodium L-lactate (50%) | 2.290 g |
| | Zinc sulfate hydrate | 0.7 mg |
| | Thiamine hydrochloride (B1) | 1.0 mg |
| | Total amount | 350 mL |

Reference Example 5

An infusion formulation was obtained in the same manner as in Reference Example 4, except that the pH thereof was adjusted to 5.1 by using acetic acid as a pH adjustor.

Reference Example 6

An infusion formulation was obtained in the same manner as in Reference Example 4, except that the pH thereof was adjusted to 4.9 by using acetic acid as a pH adjustor.

Reference Example 7

An infusion formulation was obtained in the same manner as in Reference Example 4, except that the pH thereof was adjusted to 4.7 by using acetic acid as a pH adjustor.

Reference Example 8

An infusion formulation was obtained in the same manner as in Reference Example 4, except that the pH thereof was adjusted to 4.5 by using acetic acid as a pH adjustor.

Reference Example 9

An infusion formulation was obtained in the same manner as in Reference Example 4, except that the pH thereof was adjusted to 4.3 by using acetic acid as a pH adjustor.

Test Example 8

The infusion formulations prepared in the respective Reference Examples 1 to 9 were stored for 2 weeks and 1 month under conditions of 25° C. and 60% RH, and then the thiamine content was measured by liquid chromatography. The results are shown in Table 15. In addition, the content is expressed as a percentage based on the mixed amount. As shown in the results, vitamin B1 remained stable at pH of 4.7 to 5.5 without being affected by dissolved oxygen.

TABLE 15

| Reference Example | pH | Before sterilization | After sterilization | Storage for 2 weeks | Storage for 1 month |
| --- | --- | --- | --- | --- | --- |
| 1 | 5.5 | 100 | — | 94.7 | 91.7 |
| 2 | 5.0 | 100 | — | 95.2 | 91.7 |
| 3 | 4.5 | 100 | — | 84.3 | 81.6 |
| 4 | 5.3 | 100 | 93.2 | 91.8 | 90.5 |
| 5 | 5.1 | 100 | 92.2 | 91.6 | 90.6 |
| 6 | 4.9 | 100 | 93.1 | 90.9 | 90.4 |
| 7 | 4.7 | 100 | 93.1 | 88.2 | 87.0 |
| 8 | 4.5 | 100 | 93.6 | 76.8 | 78.9 |
| 9 | 4.3 | 100 | 93.9 | 70.4 | 70.6 |

—: unmeasured

INDUSTRIAL APPLICABILITY

The present invention is a nutrition infusion for administration through a peripheral vein that contains reducing sugar, amino acids, and electrolytes and further contains a vitamin B group and vitamin C stably. The present invention can be used for medical use, as a nutrition infusion for administration through a peripheral vein that has less concern for deficiency of vitamins.

The invention claimed is:

1. A method of administering a nutrition infusion, comprising:
   providing a kit comprising a first package containing a sugar solution comprising a reducing sugar, vitamin B1, vitamin B12, and pantothenic acid and having a pH of 4.7 to 5.5, and a second package separated from the first package and containing an amino acid solution comprising an amino acid, vitamin B2, folic acid, vitamin C, biotin, and sulfite in an amount of 25 mg/L to 100 mg/L, and having a pH of 7.0 to 7.5, wherein the sugar solution and the amino acid solution are prepared such that a nutrition infusion produced by mixing only the sugar solution and the amino acid solution contains 100 μg/L to 400 μg/L of the folic acid;
   producing the nutrition infusion from the kit by mixing the sugar solution and the amino acid solution; and
   administering the nutrition infusion through a peripheral vein of a subject.

2. The method according to claim 1, wherein the reducing sugar in the sugar solution is glucose, and the sugar solution and the amino acid solution are prepared such that the nutrition infusion produced by mixing only the sugar solution and the amino acid solution has a glucose concentration of 4 w/v % to 10 w/v %.

3. The method according to claim 1, wherein the sugar solution further comprises vitamin B6, and the amino acid solution further comprises a nicotinic acid derivative.

4. The method according to claim 1, wherein the sugar solution further comprises acetic acid as a pH adjustor.

5. The method according to claim 1, wherein the sugar solution and the amino acid solution are prepared such that the nutrition infusion produced by mixing only the sugar solution and the amino acid solution has a pH of 6.5 to 7.4.

6. The method according to claim 1, wherein the sugar solution and the amino acid solution are prepared such that the nutrition infusion produced by mixing only the sugar solution and the amino acid solution further contains:
   Vitamin B1 in an amount of 1 mg/L to 10 mg/L,
   Vitamin B2 in an amount of 1 mg/L to 4 mg/L converted in terms of riboflavin,
   Vitamin B6 in an amount of 1 mg/L to 5 mg/L,
   Vitamin B12 in an amount of 1 μ/L to 10 μg/L,
   Pantothenic acids in an amount of 4 mg/L to 16 mg/L,
   Nicotinic acid derivative in an amount of 10 mg/L to 40 mg/L,
   Biotin in an amount of 25 μg/L to 100 μg/L, and
   Vitamin C in an amount of 50 mg/L to 200 mg/L.

7. The method according to claim 1, wherein
   the sugar solution further comprises sodium chloride in an amount of 0.5 g/L to 2 g/L, a calcium chloride hydrate in an amount of 0.2 g/L to 1 g/L, sodium lactate in an amount of 2 g/L to 15 g/L, a magnesium sulfate hydrate in an amount of 0.5 g/L to 2 g/L, and a zinc sulfate hydrate in an amount of 1 mg/L to 4 mg/L,
   the amino acid solution comprises the amino acid in an amount of 50 g/L to 300 g/L in terms of a free amino acid, and
   the volume ratio between the sugar solution and the amino acid solution is 2:1 to 3:1.

8. The method according to claim 1, wherein the sugar solution and the amino acid solution are prepared such that the nutrition infusion produced by mixing only the sugar solution and the amino acid solution contains L-tryptophan in an amount of 0.04 g/L to 3.0 g/L, N-acetyl-L-cysteine in an amount of 0.01 g/L to 2.0 g/L, or both.

9. The method according to claim 1, wherein the sugar solution has a pH of 4.9 to 5.5.

10. The method according to claim 1, wherein the volume ratio of the sugar solution to the amino acid solution is 2:1 to 3:1.

11. The method according to claim 1, wherein the amino acid solution has a pH of 7.0 to 7.2.

12. The method according to claim 1, wherein the amino acid solution has a pH of 7.1 to 7.5.

13. The method according to claim 1, wherein the amino acid solution has a pH of 7.1 to 7.2.

14. The method according to claim 1, wherein the sugar solution and the amino acid solution are prepared such that the nutrition infusion produced by mixing only the sugar solution and the amino acid solution further contains:
L-Isoleucine in an amount of 0.2 g/L to 14.0 g/L,
L-Leucine in an amount of 0.4 g/L to 20.0 g/L,
L-Lysine in an amount of 0.2 g/L to 14.0 g/L,
L-Methionine in an amount of 0.1 g/L to 8.0 g/L,
L-Phenyl alanine in an amount of 0.2 g/L to 12.0 g/L,
L-Threonine in an amount of 0.1 g/L to 8.0 g/L,
L-Tryptophan in an amount of 0.04 g/L to 3.0 g/L,
L-Valine in an amount of 0.1 g/L to 16.0 g/L,
L-Alanine in an amount of 0.2 g/L to 14.0 g/L,
L-Arginine in an amount of 0.2 g/L to 14.0 g/L,
L-Aspartic acid in an amount of 0.01 g/L to 4.0 g/L,
L-Glutamic acid in an amount of 0.01 g/L to 6.0 g/L,
L-Histidine in an amount of 0.1 g/L to 8.0 g/L,
L-Proline in an amount of 0.1 g/L to 10.0 g/L,
L-Serine in an amount of 0.1 g/L to 6.0 g/L,
L-Tyrosine in an amount of 0.01 g/L to 2.0 g/L,
Glycine in an amount of 0.1 g/L to 12.0 g/L, and
L-Cysteine in an amount of 0.01 g/L to 2.0 g/L.

15. The method according to claim 1, wherein the first package and the second package are formed in a container made of at least one material selected from the group consisting of polyethylene, polypropylene, and cyclic polyolefin.

16. The method according to claim 1, wherein the amino acid solution further comprises citric acid as a pH adjustor.

17. The method according to claim 1, wherein the amino acid solution further comprises citric acid such that the nutrition infusion produced by mixing only the sugar solution and the amino acid solution further contains 5 mEq/L to 15 mEq/L of the citric acid.

18. A method of administering a nutrition infusion, comprising:
administering, through a peripheral vein of a subject, a nutrition infusion prepared by mixing a sugar solution comprising a reducing sugar, vitamin B1, vitamin B12, and a pantothenic acid and having a pH of 4.7 to 5.5, and an amino acid solution comprising an amino acid, vitamin B2, folic acid, vitamin C, biotin, and sulfite in an amount of 25 mg/L to 100 mg/L, and having a pH of 7.0 to 7.5,
wherein the nutrition infusion comprises 100 μg/L to 400 μg/L of the folic acid, and the nutrition infusion has a pH of 6.5 to 7.4.

19. The method according to claim 18, wherein the reducing sugar in the sugar solution is glucose, and the nutrition infusion has a glucose concentration of 4 w/v % to 10 w/v %.

20. The method according to claim 18, wherein the sugar solution further comprises vitamin B6, and the amino acid solution further comprises a nicotinic acid derivative.

21. The method according to claim 18, wherein the sugar solution further comprises acetic acid as a pH adjustor.

22. The method according to claim 18, wherein the nutrition infusion has a pH of 6.8 to 7.4.

23. The method according to claim 18, wherein the nutrition infusion contains:
Vitamin B1 in an amount of 1 mg/L to 10 mg/L,
Vitamin B2 in an amount of 1 mg/L to 4 mg/L converted in terms of riboflavin,
Vitamin B6 in an amount of 1 mg/L to 5 mg/L,
Vitamin B12 in an amount of 1 μg/L to 10 μg/L,
Pantothenic acids in an amount of 4 mg/L to 16 mg/L,
Nicotinic acid derivative in an amount of 10 mg/L to 40 mg/L,
Biotin in an amount of 25 μg/L to 100 μg/L, and
Vitamin C in an amount of 50 mg/L to 200 mg/L.

24. The method according to claim 18, wherein the sugar solution further comprises sodium chloride in an amount of 0.5 g/L to 2 g/L, a calcium chloride hydrate in an amount of 0.2 g/L to 1 g/L, sodium lactate in an amount of 2 g/L to 15 g/L, a magnesium sulfate hydrate in an amount of 0.5 g/L to 2 g/L, and a zinc sulfate hydrate in an amount of 1 mg/L to 4 mg/L,
the amino acid solution comprises the amino acid in an amount of 50 g/L to 300 g/L in terms of a free amino acid, and
the volume ratio between the sugar solution and the amino acid solution is 2:1 to 3:1.

25. The method according to claim 18, wherein the amino acid solution further comprises citric acid as a pH adjustor.

26. The method according to claim 18, wherein the amino acid solution further comprises citric acid such that the nutrition infusion produced by mixing only the sugar solution and the amino acid solution further contains 5 mEq/L to 15 mEq/L of the citric acid.

* * * * *

UNITED STATES PATENT AND TRADEMARK OFFICE
CERTIFICATE OF CORRECTION

PATENT NO. : 9,861,575 B2  
APPLICATION NO. : 13/668558  
DATED : January 9, 2018  
INVENTOR(S) : Kazuhiro Abiko et al.

Page 1 of 1

It is certified that error appears in the above-identified patent and that said Letters Patent is hereby corrected as shown below:

On the Title Page

Item (71), the Applicant's name is incorrect. Item (71) should read:  
-- (71) Applicant: EA Pharma Co., Ltd., Chuo-ku (JP) --

Signed and Sealed this  
Fourth Day of June, 2019

Andrei Iancu  
*Director of the United States Patent and Trademark Office*